(12) United States Patent
Choi et al.

(10) Patent No.: US 10,627,402 B2
(45) Date of Patent: Apr. 21, 2020

(54) PEPTIDES FOR TARGETING GASTRIC CANCER, AND MEDICAL USE TEHREOF

(71) Applicant: UNIVERSITY OF ULSAN FOUNDATION FOR INDUSTRY COOPERATION, Ulsan (KR)

(72) Inventors: Eun Kyung Choi, Seoul (KR); Seong-Yun Jeong, Yongin-si (KR); Si Yeol Song, Seoul (KR); Kyoung Jin Lee, Seoul (KR); Seol Hwa Shin, Seoul (KR); Eun Jin Ju, Seoul (KR)

(73) Assignee: UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 0 days.

(21) Appl. No.: 16/149,142

(22) Filed: Oct. 2, 2018

(65) Prior Publication Data

US 2019/0018014 A1  Jan. 17, 2019

Related U.S. Application Data

(63) Continuation of application No. 15/527,717, filed as application No. PCT/KR2015/007943 on Jul. 29, 2015, now abandoned.

(30) Foreign Application Priority Data

Nov. 18, 2014 (KR) .................... 10-2014-0160818
Jul. 28, 2015 (KR) .................... 10-2015-0106581

(51) Int. Cl.
| | | |
|---|---|---|
| *A61K 38/08* | (2019.01) | |
| *A61K 38/10* | (2006.01) | |
| *A61K 47/00* | (2006.01) | |
| *A61K 49/00* | (2006.01) | |
| *C07K 7/06* | (2006.01) | |
| *C07K 7/08* | (2006.01) | |
| *C07K 7/00* | (2006.01) | |
| *G01N 33/58* | (2006.01) | |
| *G01N 33/00* | (2006.01) | |
| *G01N 33/574* | (2006.01) | |

(52) U.S. Cl.
CPC ....... *G01N 33/574* (2013.01); *A61K 49/0008* (2013.01); *C07K 7/08* (2013.01); *G01N 33/57446* (2013.01); *G01N 33/58* (2013.01); *A61K 47/00* (2013.01); *A61K 49/00* (2013.01); *G01N 33/00* (2013.01)

(58) Field of Classification Search
CPC .... A61K 47/00; A61K 49/00; A61K 49/0008; A61K 38/08; A61K 38/10; C07K 7/00; C07K 7/08; C07K 7/06; G01N 33/00; G01N 33/574; G01N 33/57446; G01N 33/58
USPC ........... 514/1.1, 19.2, 19.3, 21.5, 21.6, 21.7; 530/300, 327, 328, 329
See application file for complete search history.

(56) References Cited

U.S. PATENT DOCUMENTS

| | | |
|---|---|---|
| 2005/0196754 A1 | 9/2005 | Drmanac et al. |
| 2008/0305212 A1 | 12/2008 | Wong et al. |
| 2017/0224848 A1 | 8/2017 | Lu et al. |
| 2018/0110886 A1 | 4/2018 | Lu et al. |

FOREIGN PATENT DOCUMENTS

| | | | |
|---|---|---|---|
| CN | 102329374 A | 1/2012 | |
| KR | 10-2014-0123311 | * 10/2014 | ............... C07K 7/06 |
| KR | 10-2014-0123311 A | 10/2014 | |

OTHER PUBLICATIONS

KR 10- 2014-0123311 machine translation, Oct. 2014.*
International Search Report for PCT/KR2015/007943 dated Oct. 29, 2015 from Korean Intellectual Property Office.
Pastor, C. et al., "Identification of major allergens in watermelon", International Archives of Allergy and Immunology, 2009, vol. 149, p. 291-298.
Zhang, W.-J. et al., "Affinity peptide developed by phage display selection for targeting gastric cancer", World Journal of Gastroenterology, 2012, vol. 18, No. 17, pp. 2053-2060.
Uni Prot A0A0B6ZBL2, pp. 1-2. Integrated into UniProtKB/ TrEMBL Apr. 1, 2015.
Heinig et al, "Taxol: A complex diterpenoid natural product with an evolutionarily obscure origin," African Journal of Biotechnology, 2009, 8(8): 1370-1385.
Li et al, "Synthesis and Biological Evaluation of a Peptide Paclitaxel Conjugte Which Targets the Integrin alphavbeta6 ," Bioorg Med Chem, 2011, 19(18): 5480-5489.

* cited by examiner

Primary Examiner — Julie Ha
(74) Attorney, Agent, or Firm — Revolution IP, PLLC

(57) ABSTRACT

Provided is a peptide for targeting gastric cancer, a composition for diagnosing radioresponsiveness-dependent gastric cancer using the peptide, and a drug delivery use of the peptide, wherein a functional peptide capable of targeting cancer has been discovered so as to implement personalized diagnosis and treatment for individual patients having cancer, consideration of problems occurring during treatment in which treatment cases of respective patients differ due to different therapeutic responses resulting from genetic differences in the individual patients.

3 Claims, 13 Drawing Sheets

Specification includes a Sequence Listing.

IRRADIATED POPULATION (10 Gy)

NON-IRRADIATED POPULATION AS CONTROL

PEPTIDES FOR TARGETING GASTRIC CANCER, AND MEDICAL USE TEHREOF

CROSS REFERENCE TO PRIOR APPLICATION

This application is a Continuation Application of U.S. patent application Ser. No. 15/527,717 filed on May 18, 2017 under 35 U.S.C. § 120, which is the 35 U.S.C. § 371 national stage of PCT International Patent Application No. PCT/KR2015/007943 filed on Jul. 29, 2015, under 35 U.S.C. § 371, which claims priority to Korean Patent Application Nos. 10-2014-0160818 filed on Nov. 18, 2014, and 10-2015-0106581 filed on Jul. 28, 2015, which are all hereby incorporated by reference in their entirety.

BACKGROUND

The present invention relates to a peptide for targeting gastric cancer, a composition for diagnosing gastric cancer based on performance of irradiation using the peptide, and drug delivery use of the peptide.

Cells which are the smallest unit of the human body maintain the balance of cell number by cell division upon intracellular regulatory functions, cell growth, and cell death and disappear, when cells are normal. If the cells are damaged by any cause, cells may be recovered by treatment to thereby serve as normal cells. However, if cells are not recovered, cells die by themselves. A condition in which abnormal cells that do not control proliferation and inhibition thereof for a variety of reasons are excessively proliferated and also cause tumefaction and destruction of normal tissues by invading surrounding tissues and organs is defined as cancer. As such, cancer refers to cell proliferation that is not inhibited, and cancer destroys the structure and function of normal cells and organs. In this regard, it is significantly important to diagnose and treat cancer.

However, there are problems during treatment in which treatment cases of respective patients differ due to different therapeutic responses resulting from genetic differences in the individual patients having cancer. Thus, in order to effectively treat cancer patients, it is required to develop a functional targeting agent capable of targeting tumor microenvironment, which depends on radioresponsiveness, and a biomarker. Accordingly, it is possible to establish personalized diagnosis and treatment for individual patients.

In addition, drug delivery systems or targeted therapies that selectively deliver drugs to cancer cells and cancer tissues are technologies that have received much attention, because even if the same amount of an anticancer agent is used, drug efficacy may be increased while side effects of drugs on normal tissues may be significantly reduced at the same time. In addition, when such technologies are applied to gene therapy, selective delivery of virus to cancer cells can increase treatment efficacy and reduce severe side effects. For this purpose, antigens that are mainly specific to tumor cells and antibodies that target such antigens have been developed up to date. However, in the case of antibodies, there are problems including concerns of immune response and low efficiency of penetration into tissues. In the case of peptides, a molecular weight thereof is so small that there is less concern of an immune responses and the penetration of peptides into tissues is easy. Therefore, if cancer-targeting peptides are coupled with existing anticancer drugs, such resulting products can be utilized as intelligent drug vehicles that selectively deliver drugs to tumors.

The present invention, unlike screening methods that have been studied at the existing cell culture levels, establishes mouse models transplanted with a cancer tissue of an actual human, to thereby divide them into an irradiated population and a non-irradiated population as a control group. In addition, a method of screening a peptide that specifically binds to each population above is disclosed to provide a novel peptide for targeting gastric cancer and a medical use of such a novel peptide.

SUMMARY

To solve the technical problem above, the present invention provides a peptide for targeting gastric cancer and a polynucleotide encoding the peptide, the peptide including an amino acid sequence selected from the group consisting of SEQ ID NOs: 1 to 6.

In an embodiment, the present invention provides a peptide for targeting gastric cancer, the peptide including an amino acid selected from the group consisting of SEQ ID NOs: 1 to 3.

In an embodiment, the present invention provides a composition including the peptide for diagnosing gastric cancer and a composition including the peptide for diagnosing radio-reactive gastric cancer.

The present invention provides a composition including the peptide for delivering a drug.

The present invention relates to a peptide for targeting gastric, a composition for diagnosing radioresponsiveness-dependent gastric cancer using the peptide, and a drug delivery use of the peptide. Considering problems during treatment in which treatment cases of respective patients differ due to different therapeutic responses resulting from genetic differences in the individual patients having cancer, a functional peptide capable of targeting cancer has been discovered so as to establish personalized diagnosis and treatment for individual patients. Animal models similar to cancer microenvironments of actual patients having cancer are prepared and divided into irradiated populations and non-irradiated populations as a control group, to thereby test target efficiency for respective peptides that are selected by screening peptides specifically binding to the respective populations. As such, the present invention can be finally utilized in the technical development of image diagnosis for predicting responsiveness to radiotherapy, and accordingly, the development of customized targeted therapeutic agents.

BRIEF DESCRIPTION OF THE DRAWINGS

FIG. 1 includes (A) showing a patient's gastric cancer tissue distributed from the Bio Research Center (BRC, Korea), (B) showing a NOD/SCID mouse that undergoes heterotrophic transplantation into the flanks of the mouse, (C) showing a cancer tissue cut into pieces each having a size of 3×3 mm to be used for subculturing, when the size of the cancer tissue of FIG. 1B is increased up to 500 mm$^3$, (D) showing a mouse model prepared in a way that a nude mouse is anesthetized via intraperitoneal injection and undergoes heterotrophic transplantation of one piece of the cut tissues subcutaneously on the both thighs, and (E) showing irradiation of 10 grays (Gy) of radiation over the thigh portions where the cancer cell is formed, when the size of the cancer tissue is increased up to 150-200 mm$^3$. Here, a control group is not subjected to irradiation.

FIG. 10A is a schematic diagram showing linking of a peptide to a liposome including a drug encapsulated therein and also shows a chemical constitutional formula representing actually linked residues, and FIG. 10B shows results of a reduction test to calculate the number of —SH residues in a liposome before being linked to a peptide and also shows results confirming stability through verification of the size distribution after being linked to a peptide.

DETAILED DESCRIPTION

Figure 1:
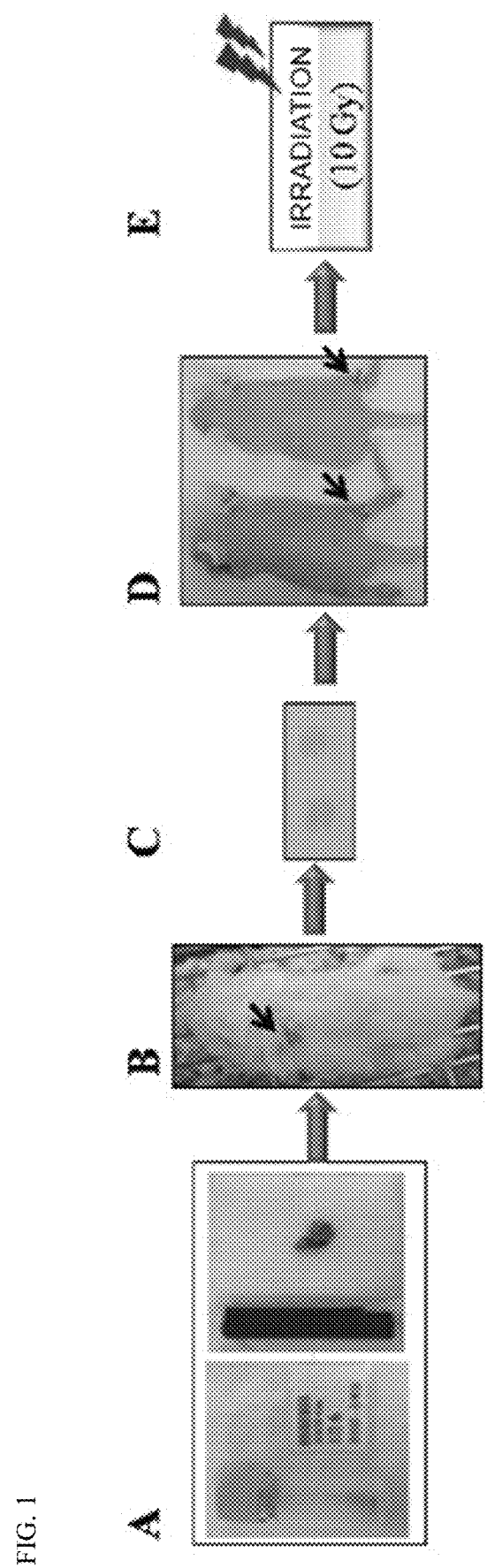
FIG. 1 is an image showing a method of establishing an irradiated animal model after transplanting an actual patient's gastric cancer tissue into a mouse according to Example 1 of the present invention, and also showing confirmation results of the established animal model.

The present invention provides a peptide for targeting gastric cancer, the peptide including an amino acid sequence selected from the group consisting of SEQ ID NOs: 1 TO 6. The above-mentioned amino acid sequences are shown in Table 1.

The peptide of the present invention is a low-molecular weight peptide consisting of 7 amino acids. Such a low-molecular weight peptide is small in size so that it can be stabilized three-dimensionally. In addition, a low-molecular weight peptide has the advantage of being able to easily pass through a membrane and to recognize a target molecule deep in tissues. Since the stability of the low-molecular weight peptide of the present invention is secured through local injection and the immunoreactivity can be minimized, there is an advantage that cancer can be diagnosed early. In addition, the mass production of the low-molecular weight peptide of the present invention is relatively easy compared that of an antibody, and the toxicity of the low-molecular weight peptide of the present invention is weak.

In addition, the low-molecular weight peptide of the present invention is has an advantage of a strong binding force to a target material compared to an antibody, and do not undergo denaturation during thermal/chemical treatment. In addition, due to a small molecular size, the low-molecular weight peptide can be used as a fused protein as being attached to other proteins. In detail, the low-molecular weight peptide can be also used as being attached to a high-molecular weight protein chain, and accordingly, can be used as a diagnosis kit and a drug delivery carrier.

The low-molecular weight peptide of the present invention can be easily prepared according to the chemical process known in the art (Creighton, Proteins; Structures and Molecular Principles, W. H. Freeman and Co., NY, 1983). As representative methods, liquid or solid phase synthesis, fractional condensation, F-MOC or T-BOC chemical method, or the like may be used (Chemical Approaches to the Synthesis of Peptides and Proteins, Williams et al., Eds., CRC Press, Boca Raton Fla., 1997; A Practical Approach, Athert on & Sheppard, Eds., IRL Press, Oxford, England, 1989), but the method is not limited thereto.

In addition, the low-molecular weight peptide of the present invention can be prepared according to a genetic engineering method. First, according to a conventional method, a DNA sequence encoding the sequence low-molecular weight peptide is prepared. Here, a DNA sequence can be prepared by PCR amplification using an appropriate primer. Alternatively, according to a standard method known in the art, a DNA sequence can be synthesized using, for example, an automatic DNA synthesizer (manufactured by Biosearch or AppliedBiosystems). Such a synthesized DNA sequence is inserted to a vector including one or more expression control sequences (for example: a promoter, an enhancer, or the like) that are operatively linked with the DNA sequence to control expression of the DNA sequence, and then, a host cell is transformed with a recombinant expression vector prepared therefrom. A resulting transformant is cultured in an appropriate medium under suitable conditions to allow the expression of the DNA sequence, so that substantially pure peptides that are encoded by the DAN sequence are recovered from the culture. Such recovery may be performed according to a method known in the art (for example, chromatography). The term 'substantially pure peptides' used herein refers to peptides that do not substantially include any protein derived from the host.

In addition, the present invention provides a peptide for targeting gastric cancer, the peptide being specific to an irradiated gastric cancer tissue and including an amino acid sequence selected from the group consisting of SEQ ID NOs: 1 to 3.

In detail, a peptide including an amino acid sequence selected from the group consisting of SEQ ID NOs: 1 to 3 specifically binds to a gastric cancer tissue, in particular, an irradiated gastric cancer tissue.

The term "target" or "specific" used herein refers to ability to specifically bind only to a gastric cancer tissue, especially an irradiated gastric cancer tissue, without binding to other normal tissues. A gastric cancer-specific peptide can specifically bind to the inside or outside of a gastric cancer tissue.

In addition, the present invention provides a polynucleotide encoding an amino acid sequence selected from the group consisting of SEQ ID NOs: 1 to 3.

The term "polynucleotide" used herein refers to a single-stranded or double-stranded polymer of deoxyribonucleotides or ribonucleotides. Such a polynucleotide includes a RNA genome sequence, a DNA sequence (for example, gDNA and cDNA), and a RNA sequence transcribed from the DNA sequence. Unless otherwise mentioned, a polynucleotide includes an analog of a natural polynucleotide.

The polynucleotide includes not only a nucleotide sequence that encodes the peptide for targeting gastric cancer, but also a sequence complementary to the nucleotide sequence, wherein such a complementary sequence includes not only a perfectly complementary sequence, but also a substantially complementary sequence.

In addition, the polynucleotide may be subjected to modifications. Such modifications include addition, deletion, non-conservative substitution, or conservative substitution of a nucleotide. The polynucleotide encoding the amino acid sequence is also interpreted to include a nucleotide sequence that exhibits substantial identity to the nucleotide sequence. The substantial identity is obtained by aligning the nucleotide sequence with any other sequences to the greatest extent and by analyzing the aligned sequence using algorithms commonly used in the art, and in this regard, the substantial identity may indicate a sequence having at least 80% homology, at least 90% homology, or at least 95% homology with the aligned sequence.

In addition, the present invention provides a composition for diagnosing gastric cancer, the composition including a peptide including an amino acid sequence selected from the group consisting of SEQ ID NOs: 1 to 6.

In addition, the present invention provides a composition for radio-sensitive diagnosing gastric cancer, the composition including a peptide being specific to an irradiated gastric cancer tissue and including an amino acid sequence selected from the group consisting of SEQ ID NOs: 1 to 3.

The term "diagnosis" used herein refers to identification of the presence or characteristic of a pathological condition. For the purpose of the present invention, the diagnosis is to identify the presence or characteristic of gastric cancer.

The diagnosis of gastric cancer using the peptide of the present invention may be performed by detecting binding of the peptide of the present invention to a corresponding tissue or cell directly obtained from blood, urine, or biopsy.

addition, to easily confirm, detect, and quantify binding of the peptide of the present invention to the gastric cancer tissue, the peptide of the present invention can be provided in a labeled state. That is, the peptide provided herein may be linked to a detectable label (for example, via covalent binding or cross-linking). The detectable label may be a chromogenic enzyme (for example, peroxidase and alkaline phosphatase), a radioactive isotope (for example $^{124}$I, $^{125}$I, $^{111}$In, $^{99}$mTc, $^{32}$P, and $^{35}$S), a chromophore, or a luminescent material or a fluorescent material (for example, FITC, RITC, rhodamine, cyanine, Texas Red, fluorescein, phycoerythrin, or quantum dots).

Similarly, the detectable label may be an antibody-epitope, a substrate, a cofactor, an inhibitor, or a affinity ligand. Such labeling may be performed during the synthesis of the peptide of the present invention, or may be additionally performed on a peptide that is already synthesized. When using a fluorescent material is used as a detectable label, cancer may be diagnosed according to fluorescence mediated tomography (FMT). For example, the peptide of the present invention labeled with a fluorescent material may be circulated into the blood, and the fluorescence by the peptide may be observed by FMT. If fluorescent is observed, it is diagnosed as cancer.

In addition, the present invention provides a composition for delivering a drug, the composition including the peptide for targeting gastric cancer.

The peptide of the present invention may be used as an intelligent drug delivery vehicle that selectively delivers a drug to a cancer tissue. If the peptide of the present invention is used in combination with drugs of the related art in terms of treatment of cancer, the peptide of the present invention selectively delivers a drug only to a cancer tissue and a cancer cell, so that drug efficacy may be increased while drug side effects on a normal tissue may be significantly reduced at the same time.

For use as the drug, any anticancer drug that is conventionally used in the treatment of cancer can be used so long as the anticancer drug is able to be linked to the peptide of the present invention. Examples of the drug include cisplatin, 5-fluorouracil, adriamycin, methotrexate, vinblastine, busulfan, chlorambucil, cyclophosphamide, melphalan, nitrogen mustard, nitreosourea, taxol, paclitaxel, docetaxel, 6-mercapropurine, 6-thioguanine, bleomycin, daunorubicin, doxorubicin, epirubicin, idarubicin, mitomycin-C, and hydroxyurea. In addition, the linking of the anticancer drug to the peptide of the present invention may be performed by a method known in the art, for example, covalent bonding, cross linking, or the like. For this purpose, the peptide of the present invention may be, if necessary, subjected to chemical modifications to the extent that the activity thereof is not lost.

Hereinafter, to promote understanding of one or more exemplary embodiments, reference has been made in detail to embodiments. The present invention, however, may be embodied in many different forms and should not be construed as being limited to the exemplary embodiments set forth herein. Rather, these embodiments are provided so that this disclosure will be thorough and complete, and will fully convey the scope of the present invention to one of ordinary skill in the art.

<Example 1> Establishment of a Mouse Model Transplanted with a Patient's Gastric Cancer Tissue Considering overcoming limitations that existing animal models transplanted with cultured cancer cells had, an ideal animal model of cancer similar to actual patient's cancer microenvironments is prepared. Then, to establish an animal model that can confirm influence of an irradiation-dependent cancer tissue, first, a mouse model transplanted with a cancer tissue that was extracted from an actual patient having gastric cancer was established. Regarding the establishment of such an animal model, the cancer tissue extracted from a patient was cultured in an NOD/SCID mouse. Once the cancer tissue was found in the NOD/SCID mouse, subculturing was carried out by using a Balb/c nude mouse, beginning from the next subculturing. In detail, after an NOD/SCID mouse was anesthetized via intraperitoneal injection of anesthetics, the cancer tissue was cut into pieces each having a size of 3×3 mm. Next, each of both flanks of the NOD/SCID mouse was transplanted with a piece of the cut cancer tissues, treated with a mixed solution of 100 µl of 100 IU/ml penicillin, 100 µg/ml streptomycin, 100 µg/ml gentamicin, and 2.5 µg/ml amphotericin B antibiotics, and then, sutured. The NOD/SCID mouse was recovered on a heating pad (for about 2 hours). Afterwards, the formation and growth of tumors were observed every week. When the cancer tissues grew to a size of 400-500 mm$^3$, the cancer tissues were separated and cut into pieces each having a size of 3×3 mm for subculturing. Next, for next subculturing, a nude mouse was anesthetized via intraperitoneal injection of anesthetics, and a piece of the cut cancer tissues was transplanted subcutaneously on the right thigh of the nude mouse. A transplantation site was changed from the flank to the both thighs so that irradiation can be locally done without affecting other organs during irradiation. That is, a mouse model in which a cancer tissue that underwent subculturing and was re-transplanted up to four times was formed was established. The growth of the cancer tissue was observed for about a month (4 weeks), and when the size of the cancer tissue was increased to about 200 mm$^3$, only the cancer tissue was locally irradiated with 10 grays (Gy) of radiation. After having recovery time for no longer than 24 hours, in vivo peptide screening was performed. Here, as a control group in an irradiated population, a mouse model that was not irradiated among the same mouse models was used to screen a peptide. The results of the establishment of such a mouse model are shown in FIG. 1.

Figure 2:
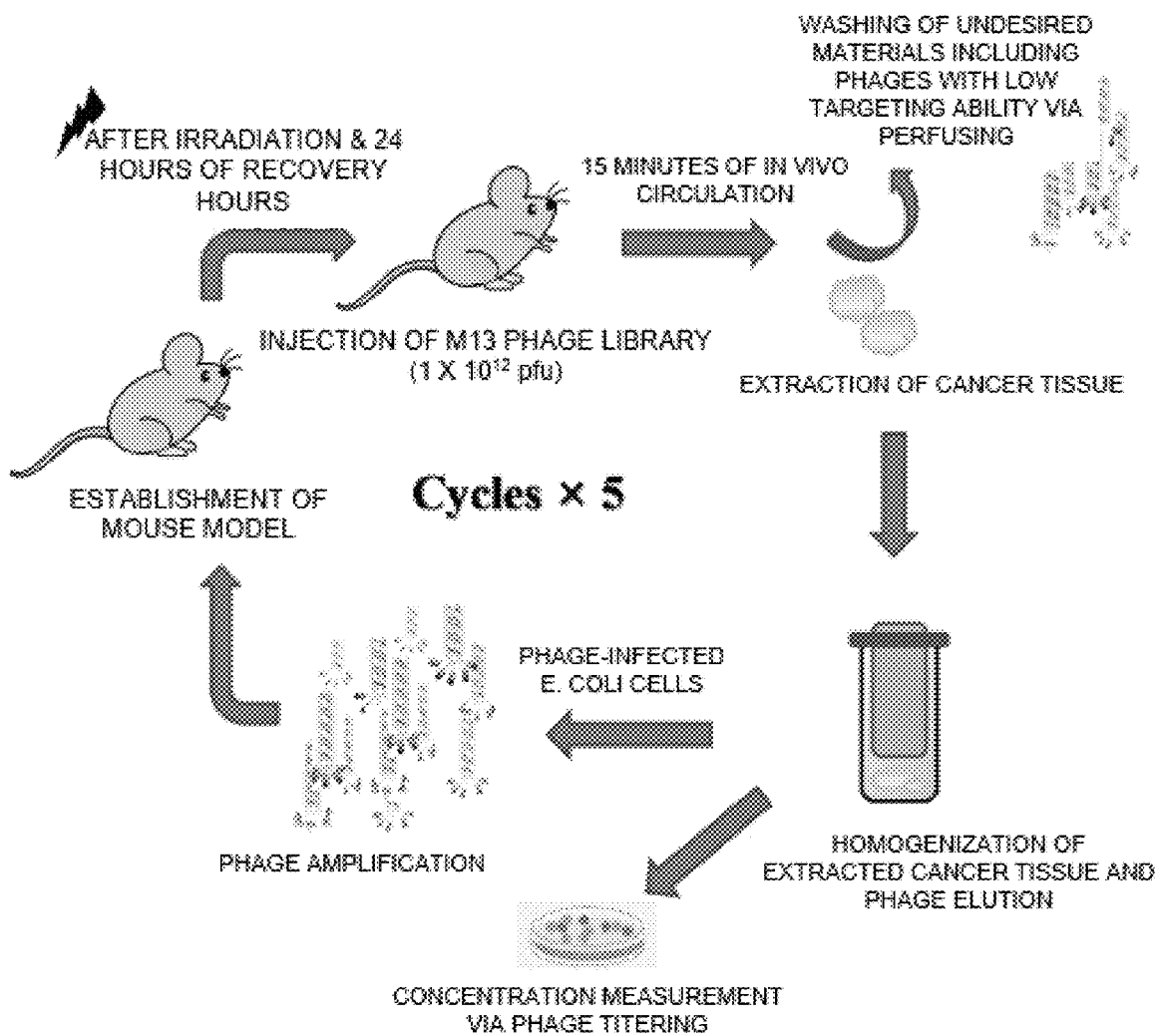
FIG. 2 shows a biopanning scheme for identifying a sequence of a peptide, which targets a gastric cancer tissue of an irradiated in vivo patient, by using an M13 phage display method according to embodiments of the present invention.
Figure 3:
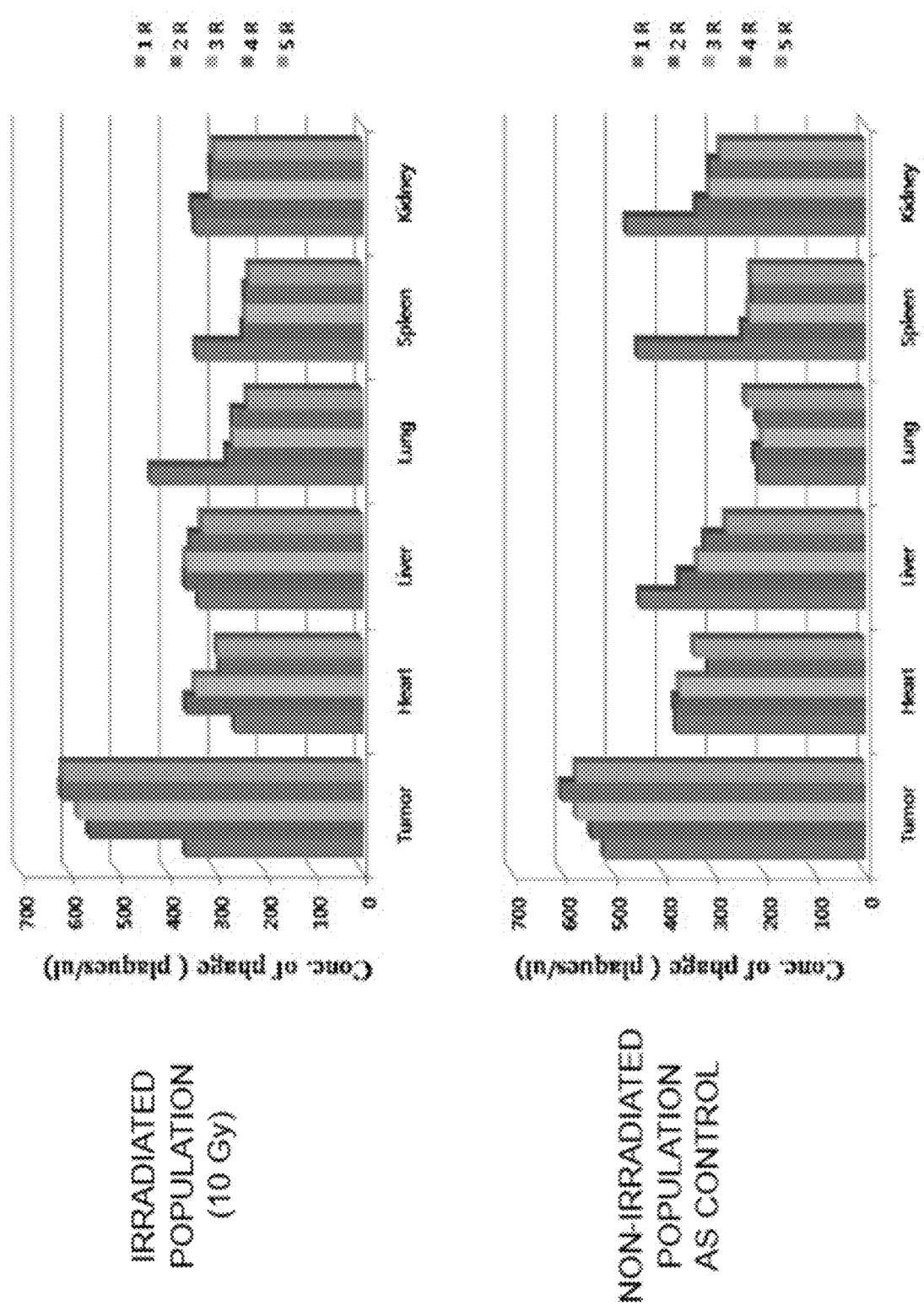
FIG. 3 shows results of comparing phage concentrations obtained by eluting phages after extracting heart, lung, liver, spleen, kidney, and tumor during biopanning process performed five times.

<Example 2> In Vivo Screening of M13 Phage Peptide Library—In Vivo Phage Display Regarding the mouse model established according to Example 1, i.e., a radio-sensitive xenograft mouse model transplanted with a patient's gastric cancer tissue, a method for identifying a peptide having high specificity during in vivo peptide screening using a random loop peptide library was designed. For use as the library, a loop peptide library manufactured to have about 2.7 billion different amino acids sequences via random array of 7 amino acids [(i.e., a library fused with an M13 phage gp3 minor coat protein)-Ph.D™ phage display peptide library kit, New England Biolabs (NEB)] was purchased. To screen a peptide showing specific binding to the irradiated gastric cancer tissue in the established mouse model, a M13 phage peptide library (i.e., a library fused with an M13 phage gp3 minor coat protein and consisting of 7 amino acids having about 2.7 billion different amino acids sequences) was injected into the tail vein of the mouse so that e M13 phage peptide library was circulated in vivo for 15 minutes (also known as a method of binding an in vivo cancer tissue with an M13 phage peptide library). Then, during this process, a peptide-expressing phage specifically binding to the cancer tissue was selected with different washing conditions. Such a screening scheme is shown in FIG. 2. In detail, FIG. 2 an M13 phage screening scheme for screening a cancer tissue-targeting peptide, wherein (1) a mouse model in which a cancer tissue was formed on the right hind leg was established, (2) a phage library in which a loop peptide library consisting of 7 amino acids was expressed on a surface of a M13 phage was injected into the tail vein of the mouse to allow circulation of the phage library, (3) phages were washed under a variety of washing conditions, and (4) phages were obtained by eluting finally targeted phages. The eluted phages infected *Escherichia coli*, and were injected again into the tail vein of the mouse to allow circulation of the phages. By repeating such cycles under washing conditions with high intensity, a process of screening phages having high specificity and a strong binding strength was repeatedly performed (also known as biopanning). Biopanning was performed five times per cycle so that a phage expressing a sequence of a peptide specifically binding to the patient's in vivo gastric cancer tissue was obtained. To confirm whether the peptide-expressing phage actually targeted the cancer tissue only, other in vivo organs were also subjected to comparison. That is, for every biopanning, phages were eluted from each of extracted heart, lung, liver, spleen, kidney, and cancer tissue, and the phage concentration was measured for comparison. The results of the comparison are shown in FIG. 3. Finally, the obtained phages infected *E. coli* ER2738 cells that are host cells, and were subjected to amplification in an LB medium. Then, 100 phage plaques were selected randomly from each of an irradiated population (experimental group) and a non-irradiated population (control group), and the M13 phage genomic DNA (single-stranded circular DNA) was separated and purified to identify a gene sequence, thereby identifying an amino acid sequence of a peptide expressed in a phage-surface protein (e.g., a gp3 minor coat protein) and targeting the cancer tissue. The results of the identification are shown in Table 1. Table 1 shows a summary of sequences discovered from each of the irradiated (experimental group) and the non-irradiated population (control group) by using the Clustal X program for sequence analysis.

TABLE 1

| Group | No. | Peptide sequence |
|---|---|---|
| Irradiated population (10 Gy) | P1 | TVRTSAD (SEQ ID NO: 1) |
| | P2 | RYVGTLF (SEQ ID NO: 2) |
| | P3 | NRGDRIL (SEQ ID NO: 3) |
| Non-irradiated population as control | W1 | NWGDRIL (SEQ ID NO: 4) |
| | W2 | QRSLPSL (SEQ ID NO: 5) |
| | W3 | DVWHSAY (SEQ ID NO: 6) |

Figure 4:
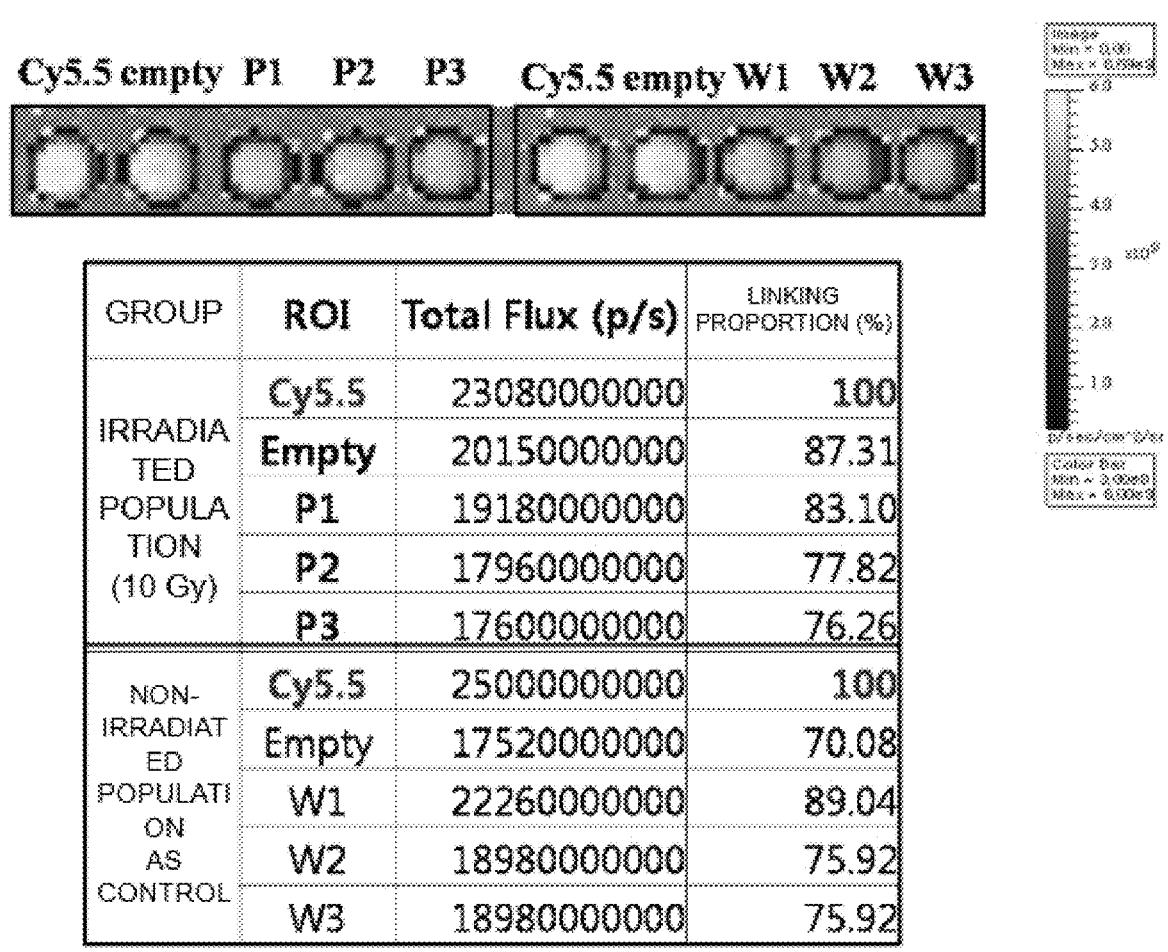
FIG. 4 shows results of a linking proportion between a Cy5.5 fluorescent probe and a phage by calculating phages of the same concentration after a discovered peptide-expressing phage of the present invention is amplified in terms of linking with the Cy5.5 fluorescent probe, and by calculating region of interest (ROI) values in connection with linking between the Cy5.5 fluorescent probe and the phage.

<Example 3> In Vivo Imaging for Confirming Targeting Ability of a Loop Peptide-Expressing Phage Regarding a Patient's Gastric Cancer Tissue To verify, based on in vivo imaging, whether the obtained phage expressing a loop peptide has exhibited specific binding ability following amplification and to confirm targeting efficiency of the obtained phage, a process of linking a fluorescent probe was performed first. In particular, 1 μg/μl of N-hydroxysuccinimide esters of Cy5.5 (Amersham) was added to 1 mL of bicarbonate buffer (pH 8.3) having the phage concentration of $10^{11}$ plaque forming units (pfu), and then, in a condition where a dark environment was maintained, 3 a phage-surface protein was linked to the Cy5.5 fluorescent probe at room temperature for 3 hours. That is, loop peptide-expressing phages to which the Cy5.5 fluorescent probe was linked were each obtained by precipitation with 170 μl of 20% (w/v) PEG 8000/2.5 M NaCl solution and purification. To determine a proportion of the Cy5.5 fluorescent probe linked to each of the finally obtained phage samples, an IVIS spectrum imaging system (Xenogen) was used for measurement, and region of interest (ROI) values were determined using the software program of a corresponding device. Accordingly, it was confirmed that the Cy5.5 fluorescent probe was linked to each of the phage samples at almost the same linking proportion. The corresponding results above are shown in FIG. 4.

After each of the prepared phages expressing the loop peptide was injected into the ratio-sensitive xenograft mouse model of Example 1 and the control group through the vein tail of the mouse, images were measured for 2 days immediately after the injection, thereby confirming images showing in vivo circulation of the peptide and the targeting of the peptide only in the cancer tissue while the targeting to other organs and tissues gradually disappeared. In this regard, the peptide was proved to completely target the in vivo gastric cancer tissue. In addition, the excellent targeting ability of the peptide sequence that was identified by biopanning according to Example 2 was resulted from the in vivo imaging and showed in FIG. 5. In addition, to verify which part of the cancer tissue was targeted by each of the loop peptide-expressing phages via ex vivo imaging, only the cancer tissue was separated and extracted, and the whole cancer tissue itself and the respective cancer tissue were subjected to fragmentation into several pieces. The imaging results obtained therefrom are shown in FIG. 6.

Figure 5:
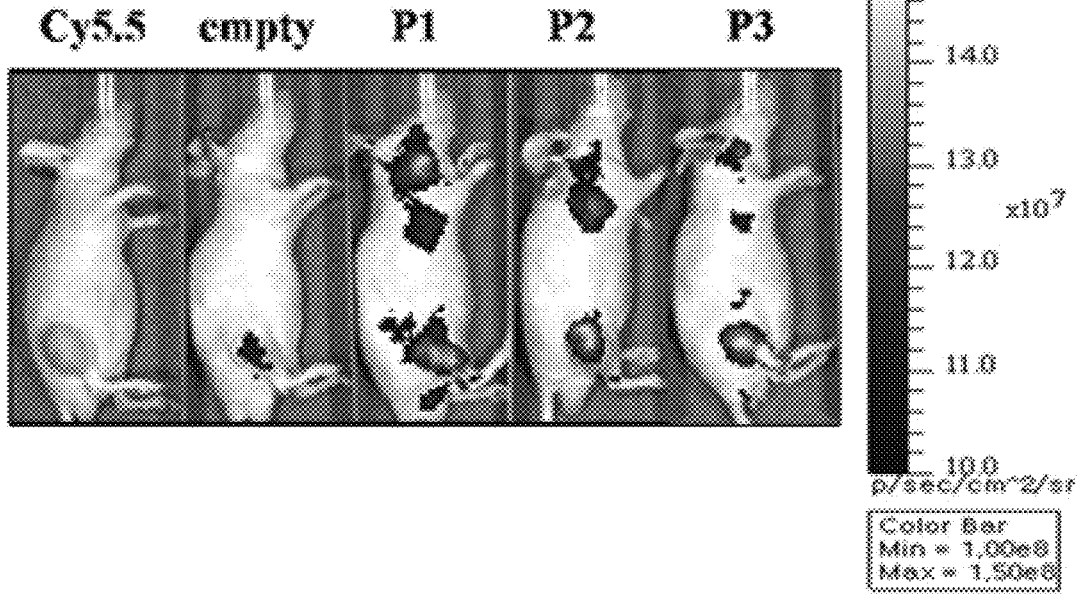
FIG. 5 shows results confirming specific binding to in vivo gastric cancer tissue based on images on the $2^{nd}$ day after injecting a peptide phage labeled with a Cy5.5 fluorescent probe into each mouse mode.
Figure 5:
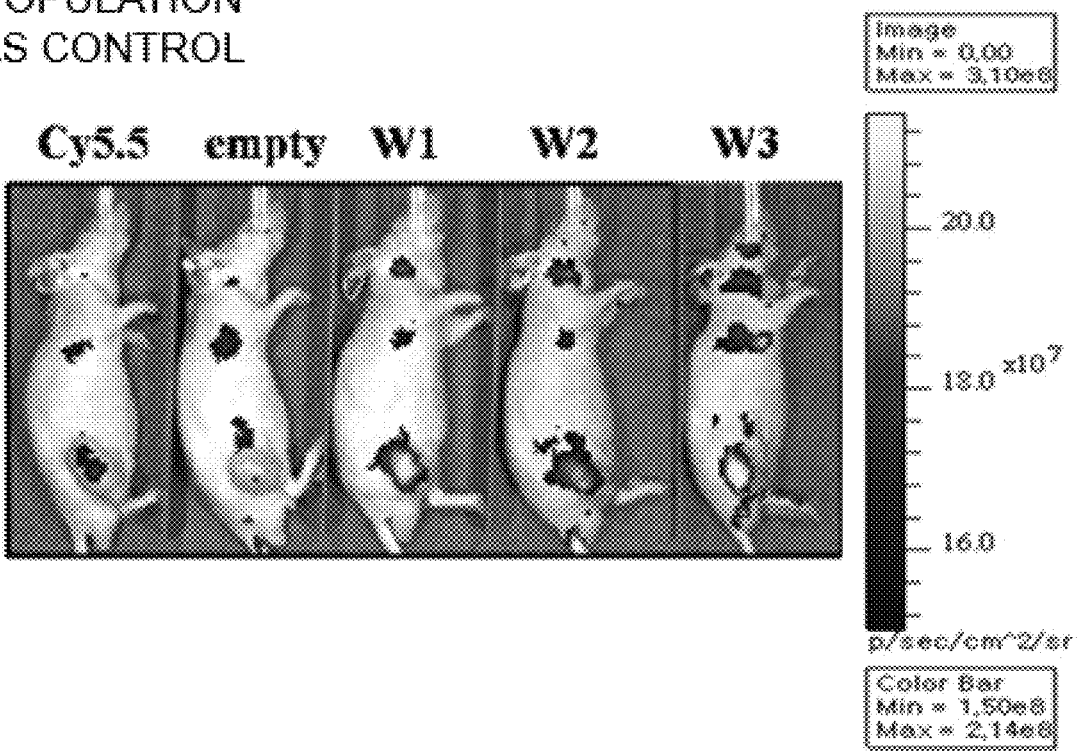
Figure 6:
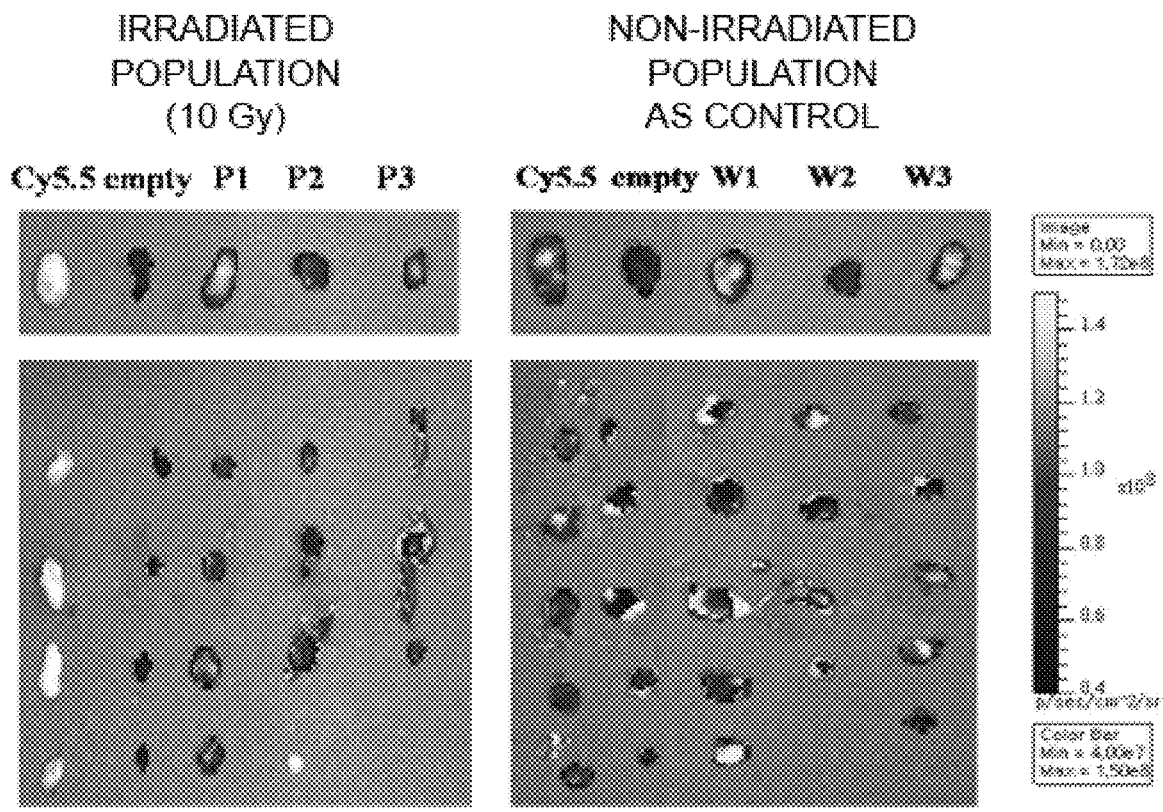
FIG. 6 shows results confirming fluorescence intensity of cancer tissue after only cancer tissue is extracted and also confirming places where fluorescence is located on cancer tissue that is equally divided, as in vivo image confirmation is completed on the $2^{nd}$ day.

To compare targeting efficiency more accurately based on the results of FIGS. 5 and 6, the pieces of the extracted cancer tissue the pieces of the extracted cancer tissue were collected independently, and phages bound to the cancer tissues were eluted. The concentration of each of the eluted phages was measured according to titering, and due to different size and weight of the extracted cancer tissue, the weight of each cancer tissue was also measured in terms of establishing numerical standardization. In this regard, the amount of the identified phages was calculated relative to the weight of the cancer tissue. In addition, to more accurately quantify each imaging result, the in vivo imaging and the ex vivo imaging were confirmed by measuring ROI values that were determined using the IVIS spectrum (Xenogen) program, and the results thereof are shown in Table 2.

TABLE 2

| Group | Sample | Sequence | pfu/mg | in vivo ROI | ex vivo ROI |
|---|---|---|---|---|---|
| Irradiated population (10 Gy) | Cy5.5 | — | — | 1.00 | 1.00 |
| | Empty | — | — | 7.37 | 24.58 |
| | P1 | TVRTSAD | 25.3 | 16.44 | 70.66 |
| | P2 | RYVGTLF | 6.3 | 9.05 | 38.83 |
| | P3 | NRGDRIL | 18.6 | 19.83 | 77.85 |
| Non-irradiated population as control | Cy5.5 | — | — | 1.00 | 1.00 |
| | Empty | — | — | 0.95 | 0.54 |
| | W1 | NWGDRIL | 11.8 | 1.86 | 2.08 |
| | W2 | QRSLPSL | 18.2 | 2.19 | 2.68 |
| | W3 | DVWHSAY | 8.1 | 1.90 | 3.54 |

Figure 7:
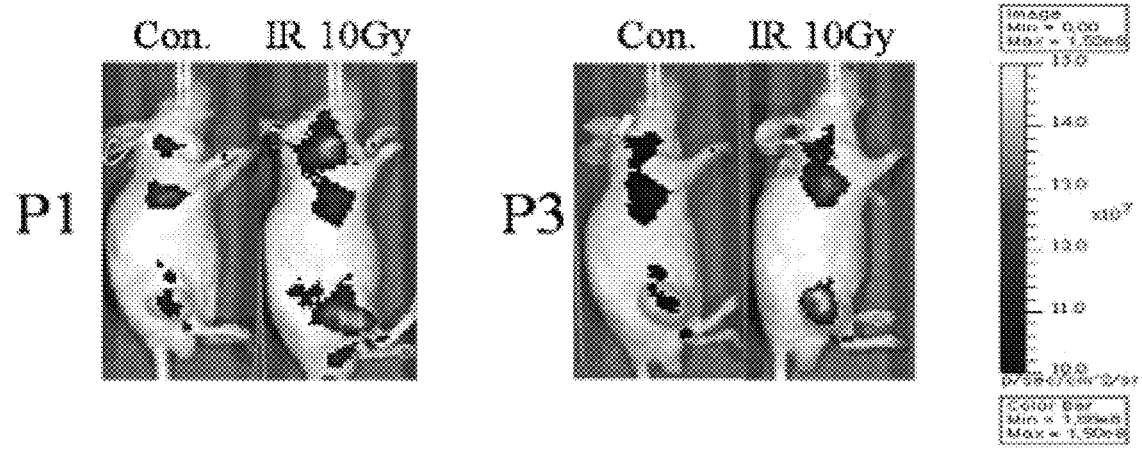
FIG. 7 shows a schematic diagram for observing changes in targeting ability of a peptide phage of the present invention as being selected depending on irradiation. In detail, after a patient's gastric cancer tissue is transplanted, mouse models in which the size of the cancer tissue is increased up to 150-200 $mm^3$ are divided into 1) irradiated mouse models and 2) irradiated mouse models with 2 grays (Gy) of radiation. After having recovery time is provided for no longer than 24 hours to the mice irradiated with 10 Gy of radiation, a selected peptide phage sample was injected thereto, and in vivo imaging are examined until the $2^{nd}$ day of the injection.

<Example 4> In Vivo Imaging for Confirming Selectively Binding Peptide Sequence Upon Irradiation To confirm whether 3 peptide sequences identified in Example 3 were responsive to cancer microenvironments during irradiation, the targeting efficiency of these irradiation-dependent peptide sequences was confirmed. In detail, in the presence of differences only in irradiation in the same mouse model transplanted with the patient's gastric cancer, targeting of the peptide which was dependent upon cancer microenvironments was subjected to verification. Accordingly, as in the mouse model established in Example 1, mice in which tumor was formed by transplantation of a patient's gastric cancer tissue were selected. Among the selected mice, only some of them were irradiated to thereby establish a control group and an experimental group. In the same manner as in Example 3, the selected phages expressing the peptide were amplified and fluorescent labeling was also performed thereon, The same sample was injected into an irradiated mouse group and a control group thereof, thereby obtaining images for the last two days. Consequently, when comparing targeting in the irradiated mouse group with that in the control group, the two groups showed differences in the targeting efficiency. The imaging measurement results of the present embodiment are shown in FIG. 7. As shown in FIG. 7, the control group including the mouse model transplanted with the patient's gastric cancer tissue showed low targeting efficiency, whereas the irradiated mouse model including the same mouse model transplanted with the patient's gastric cancer tissue showed specific binding ability through images.

Figure 8:
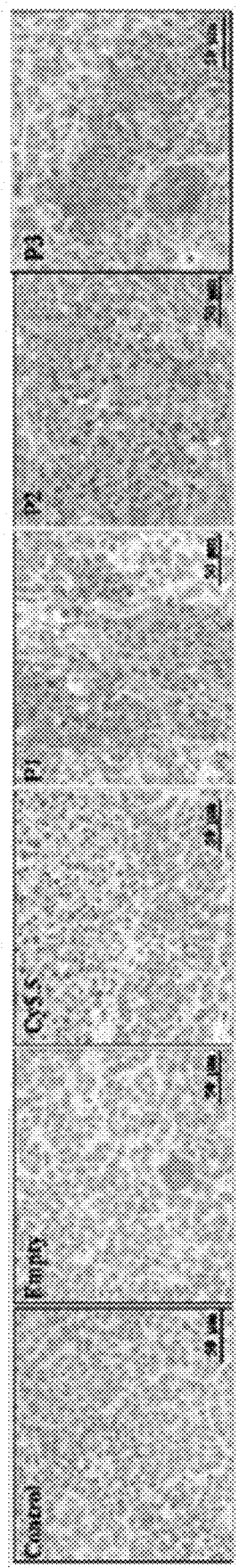
FIG. 8 shows results verifying specific binding ability of a peptide sequence discovered in each population through immunohistochemistry.
Figure 8:
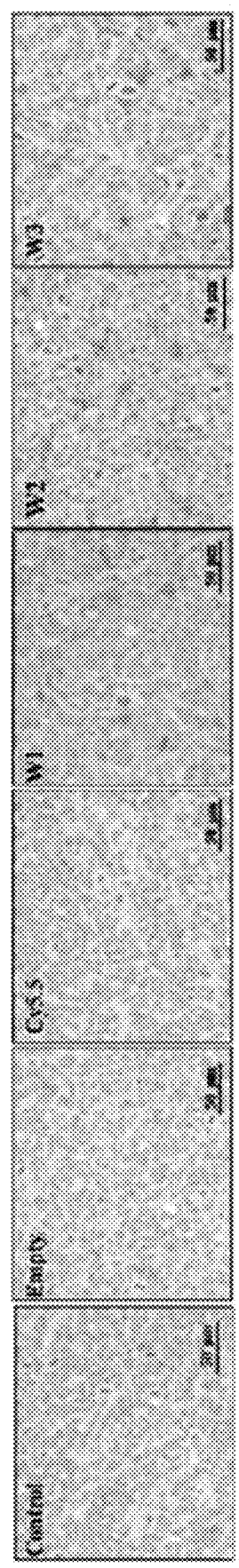

<Example 5> Histological Verification of Selective Binding Ability of a Discovered Peptide To verify histological targeting ability of the selected peptide (three sequences per population), each population was injected via the tail vein. After 24 hours, cancer tissues of each population were extracted to prepare paraffin blocks and slices. In detail, (1) the extracted cancer tissues were immersed in a formaldehyde solution at room temperature for 24 hours in terms of for immobilization. Then, following a dehydration process, paraffin was added to the solution through penetration to form paraffin blocks. Afterwards, microtome was used to manufacture slices having a thickness of 3 μm. To perform real immunohistological staining, (2) following a deparaffinization process performed on the slices, (3) an unmasking process was performed so that structures of various proteins immobilized to the tissue slices were recovered to restore sites where antibodies normally bind. Sequentially, (4) a blocking process was performed using a 5% BSA solution, primary antibodies were bound (wherein the antibodies used herein were anti-mouse M13 IgG recognizing M13 phage capsid proteins), (6) and secondary antibodies were bound while HRP was bound. Afterwards, (7) sites where phages were present were stained using DAB development, (7) the nuclei of the phages were stained with hematoxylin, and (8) a dehydration process was performed thereon. Once completed, mounting was performed so that the tissue slices that were immunohistochemically stained were permanently preserved. The results of immunohistochemical staining performed as described above are shown in FIG. 8.

Figure 9:
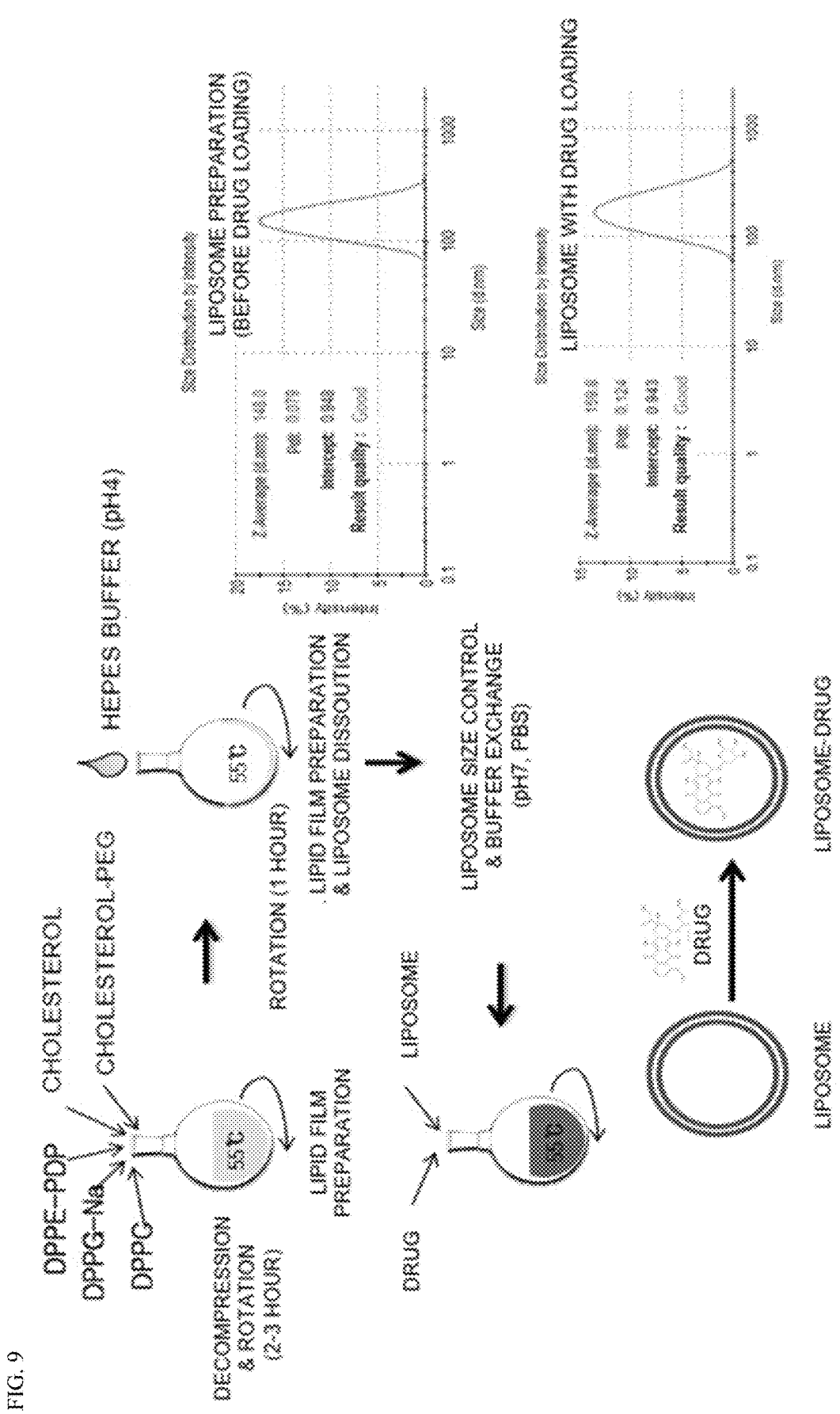
FIG. 9 shows preparation of a liposome, a drug encapsulation process and optimization thereof. As a result of verifying a liposome manufacturing process, a drug encapsulation process, and size distribution of drug, it is confirmed that there is no difference in size before and after drug encapsulation and that drugs are evenly distributed.

<Example 6> Liposome Preparation, Drug Encapsulation, and Peptide-Liposome Linking Process In detail, five lipids constituting a liposome, such as dipalmitoylphosphatidylcholine (DPPC, concentration of 50 mM), dipalmitoylphosphatidylglycerol (DPPG-Na, concentration of 50 mM), N-[3-(2pyridinyldithio)-1-oxopropyl]-L-α-dipalmitoylphosphatidylcholine (DPPE-PDP, concentration of 50 mM), cholesterol (concentration of 200 mM), and cholesterol-PEG (concentration of 200 mM), were each dissolved in an organic solvent containing methanol and chloroform (prepared at a ratio of 1:1). DPPG-Na which does not melt at room temperature was completely dissolved at 55° C. for more than 30 minutes. Each of the five dissolved lipids was added to a round-bottom flask so as to prepare a mixed solution containing DPPC:DPPE-PDP:DPPG-Na:cholesterol-PEG:cholesterol at a ratio of 15:15:30:4:36. The round-bottom flask was rotated at 55° C., and was pressurized for about 2 to 3 hours to volatilize the organic solvent therefrom. Meanwhile, a thin lipid film was formed within the round-bottom flask. When a white thin film was formed within the round-bottom flask, the organic solvent remained at room temperature was completely volatilized, so that only a pure lipid film remained. Afterwards, to prepare a liposome using the pure lipid film, 3 ml of HEPES (10 nM, pH 4) buffer was added thereto, and the round-bottom flask was rotated in a thermostat (55° C.) for 1 hour to dissolve the pure lipid film. To dissolve it sufficiently, a vortex was used to strongly shake the round-bottom flask, so that the pure lipid film was able to be completely dissolved without leaving any agglomerate. To make the size of the prepared liposome uniform, a nitrogen gas extruder and a poly-carbonate filter were used to filter the liposome through a filter with fine holes, wherein the fine holes used herein had a diameter of 800 nm, 400 nm, 200 nm, and 100 nm in the stated order. Considering accurate size and uniformity of the liposome, a filter having a diameter of 200 nm and a filter having a diameter of 100 nm were used twice or several times for extrusion. To load a drug into the extruded liposome, the buffer containing the liposome dissolved therein was replaced with PBS (pH 7.0) using a Sephadex column. Accordingly, the resulting liposome was dissolved in the buffer such that the inside of the liposome had pH 4.0 and outside thereof had pH 7.0. The liposome resulting from the completion of buffer replacement and doxorubicin dissolved in buffer having pH 7.0 were mixed in a round-bottom flask. Then, to encapsulate the drug dissolved in the buffer having pH 7.0 within the liposome having pH 4.0 by a concentration gradient, the round-bottom flask was rotated in a bath at 60° C. for 20 minutes. Then, to isolate the remaining non-encapsulated drug, a pure liposome including the drug encapsulated therein was purified using a Sephadex column. According to the Dinamic light scattering; DLS method, the drug delivery carrier was optimized by measuring the size and stability of the finally prepared drug-encapsulated liposome. The results of the drug delivery process and optimization thereof described above are shown in FIG. 9.

Figure 10A:
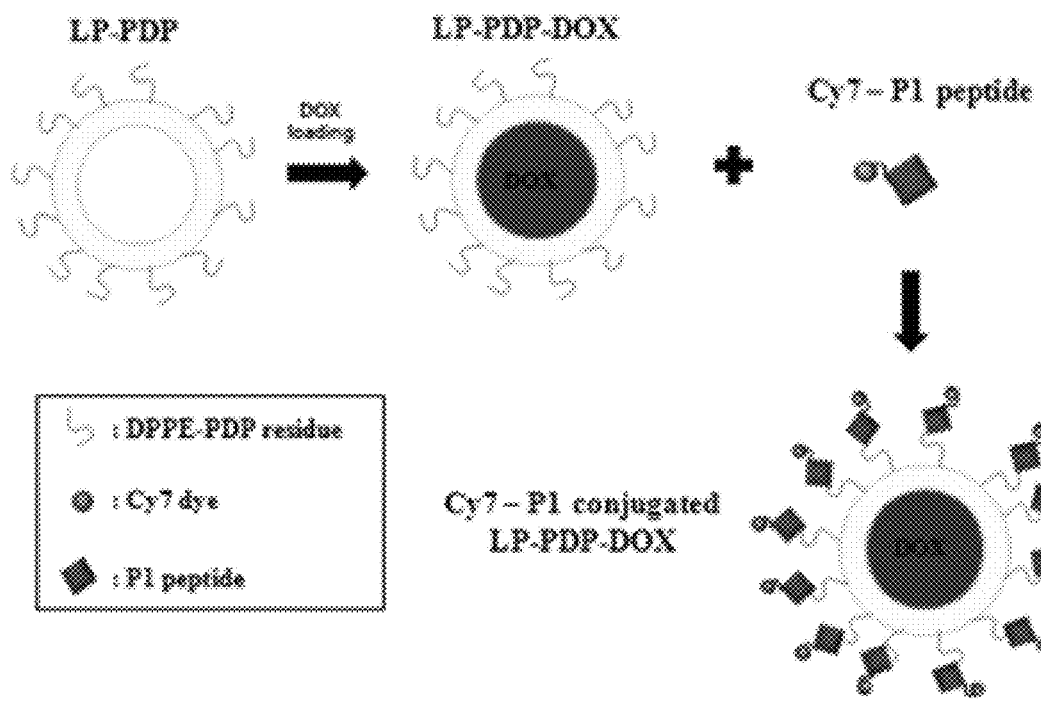
FIG. 10A and FIG. 10B show results of linking a peptide to a liposome including to a liposome including a drug encapsulated therein.
Figure 10A:
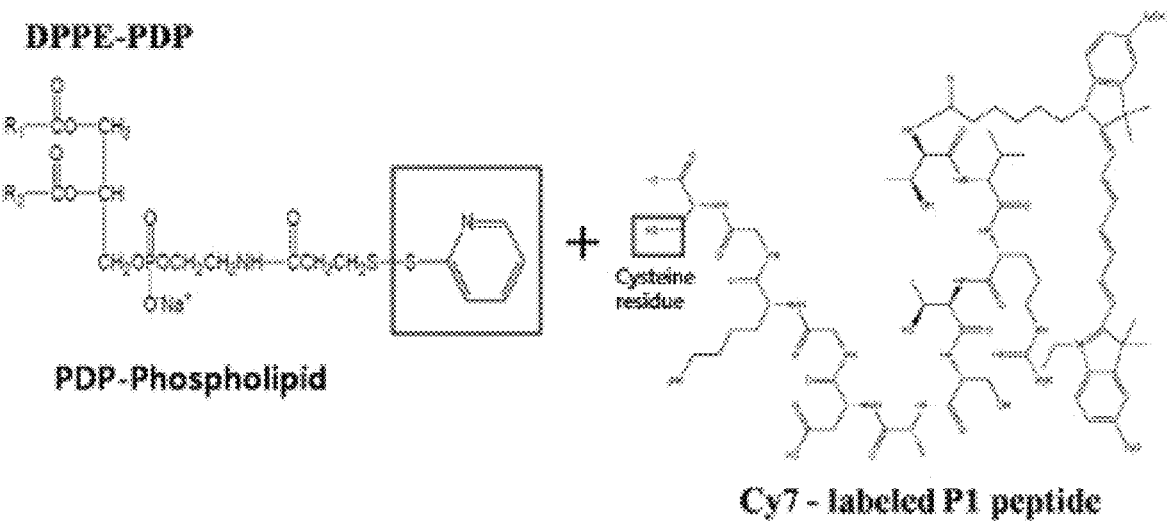
Figure 10B:
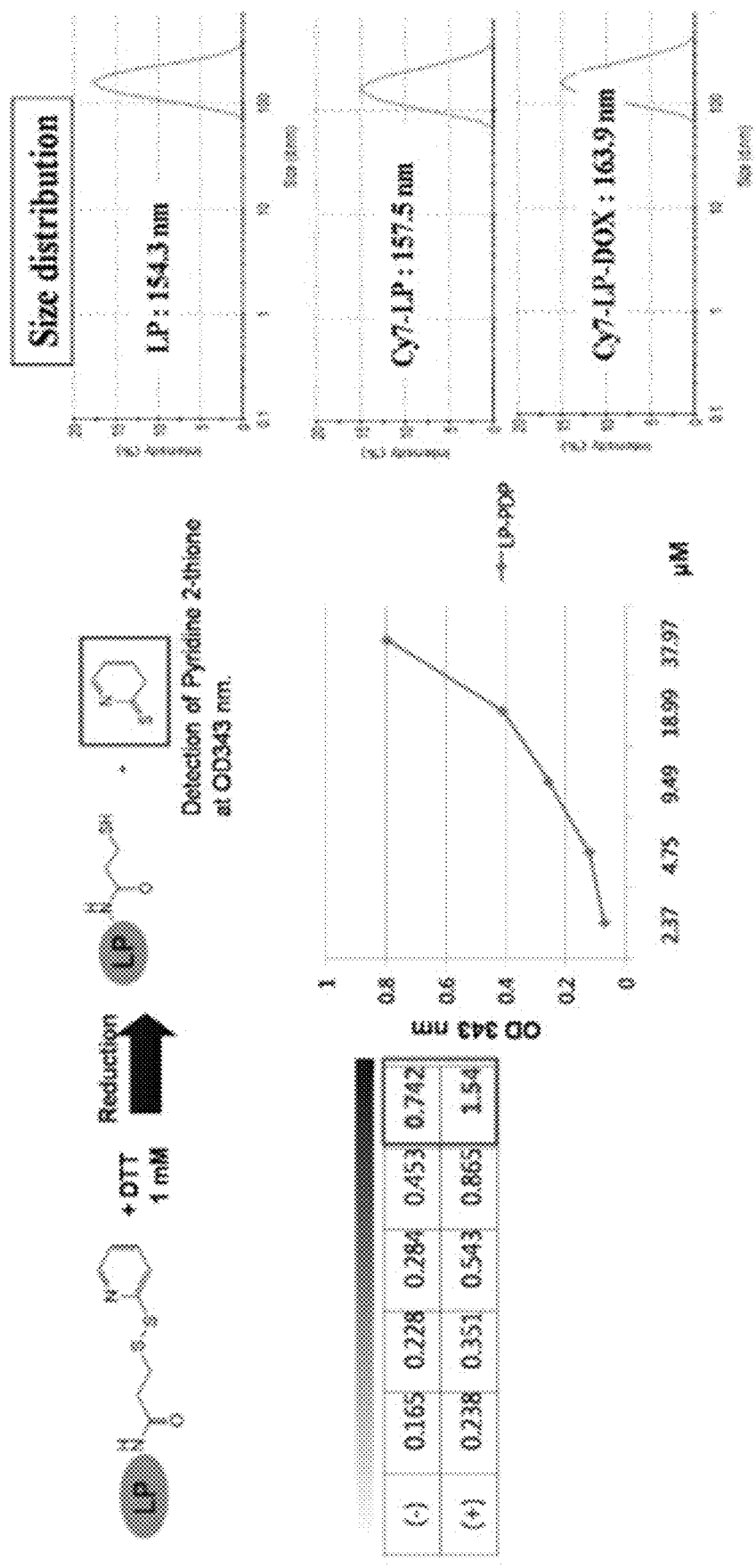

Among the peptides verified in Example 5, the peptide having 'TVRTSAD' sequence was synthesized by a request, and ligated with the drug-encapsulated liposome of Example 6. Accordingly, a peptide in which the C-terminal of the 'TVRTSAD' was linked with a Cy7 fluorescent probe and the N-terminal of the 'TVRTSAD' was free from any process to be linked with a liposome was prepared by a request from AnyGen Inc. (South Korea). The residue of the N-terminal of the prepared peptide was processed to be linked with a thiol group (—SH) of a liposome via a disulfide bond. Before performing linking with the liposome, the number of the thiol group of the liposome was counted, and a liposomal reduction test was conducted so as to link the liposome to the peptide depending on the ratio of the thiol group. DTT 1 mM was added and pyridine 2-thione was measured at $OD_{343}$ nm, to count the number of the thiol group of the liposome. Afterwards, to link the liposome with the peptide, the liposome and the peptide were mixed at a molar ratio of 1:1.5 to allow a reaction for 2 hours at room temperature. Then, to isolate unreacted (unlinked) peptide, the liposome linked with a pure peptide was purified using a Sephadex column. Afterwards, to verify that there is no change in the size and stability of the liposome before and after being linked with the peptide, the verification was demonstrated according to the Dinamic light scattering; DLS method, and the results are shown in FIG. 10.

<Example 7> Verification of Targeting Ability of Peptide-Linked Liposome and Validation of New Concept Anticancer Drug To verify whether the drug carrier of Example 6 in which the 'TVRTSAD' sequence was linked to the drug-encapsulated liposome actually played a function in the living body, in vivo imaging was performed. In detail, the radio-sensitive xenograft mouse model of Example 1 and the control group were each injected through the vein tail of the mouse, and images were measured for 2 days immediately after the injection, thereby confirming that images showing in vivo circulation of the peptide and the targeting of the peptide only in the cancer tissue while the targeting to other organs and tissues gradually disappeared. In this regard, the peptide was proved to completely target the in vivo gastric cancer tissue. The results of the in vivo imaging are shown in FIG. 11.

In addition to the in vivo imaging, in vivo tumor growth delay was also performed to validate the peptide as a target drug delivery carrier. The radio-sensitive xenograft mouse model of Example 1 and the control group were established, and once the tumor size was increased to about 100 mm$^3$, grouping was performed thereon. In this regard, a total of 5 groups, i.e., 1; PBS, 2; irradiation (2 Gy), 3; DOX(2 mg/kg)+irradiation (2 Gy), 4; LP-DOX (2 mg/kg)+irradiation (2 Gy), 5; P1(peptide)-LP-DOX (2 mg/kg)+irradiation (2 Gy), were prepared. Here, test group was designated as Group 5 while the control groups were designated as Groups 1 to 4 for observation. Each group included 5 mice (n=5). Compared to the control groups, the test group (i.e., Group 5) showed that the tumor size was significantly small, and accordingly, the results of validation of a new concept anticancer drug are shown in FIG. 12.

Figure 11:
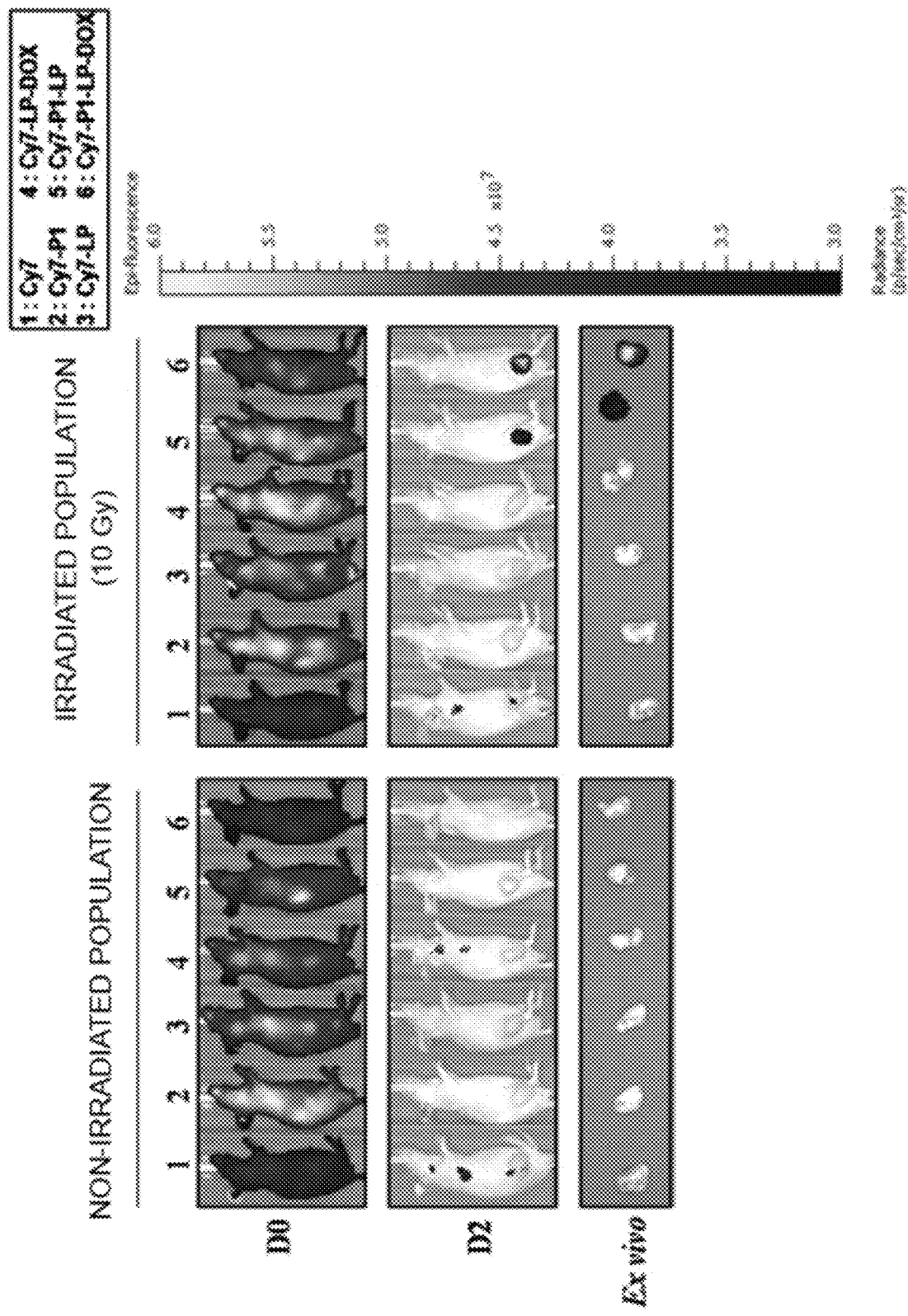
FIG. 11 shows in vivo imaging results for verifying targeting ability of a material in which a peptide is linked to a liposome including a drug encapsulated therein. It is confirmed that only a liposome linked to a peptide is targeted in an irradiated mouse.
Figure 12:
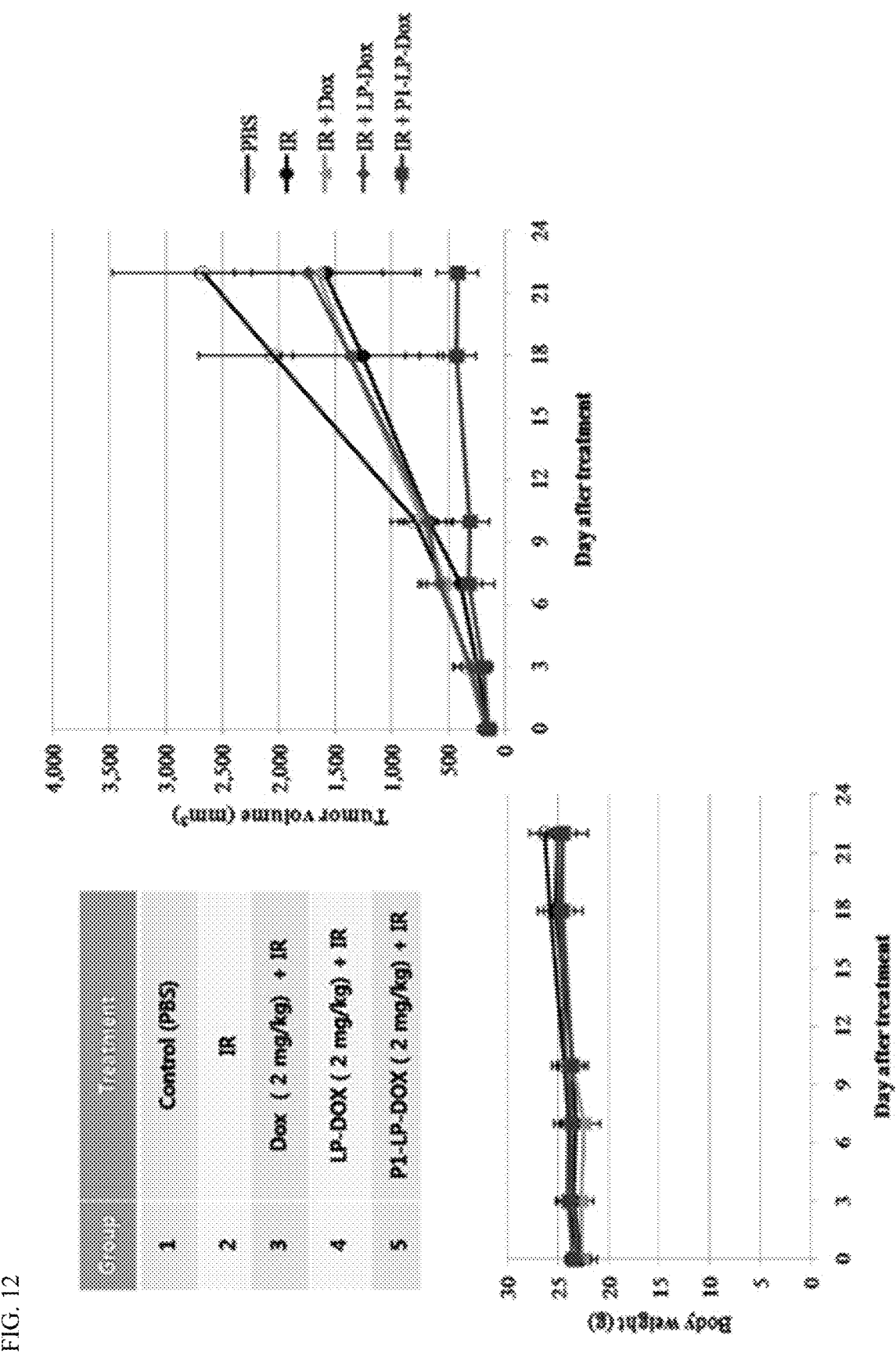
FIG. 12 shows in vivo tumor growth delay results for verifying possibility of a material in which a peptide is linked to a liposome including a drug encapsulated therein to be used as an anticancer drug. In this regard, only a liposome linked to a peptide and including a drug encapsulated therein is proved to be effective in treating tumors in an irradiated group.

As verified in FIGS. 11 and 12, the material linked with the corresponding peptide and the drug-encapsulated liposome were verified to be utilized in the in vivo imaging and the in vivo tumor growth delay, and accordingly, the possibility of the material as a new concept anticancer drug that can simultaneously diagnose and treat cancer was proved.

Figure 13:
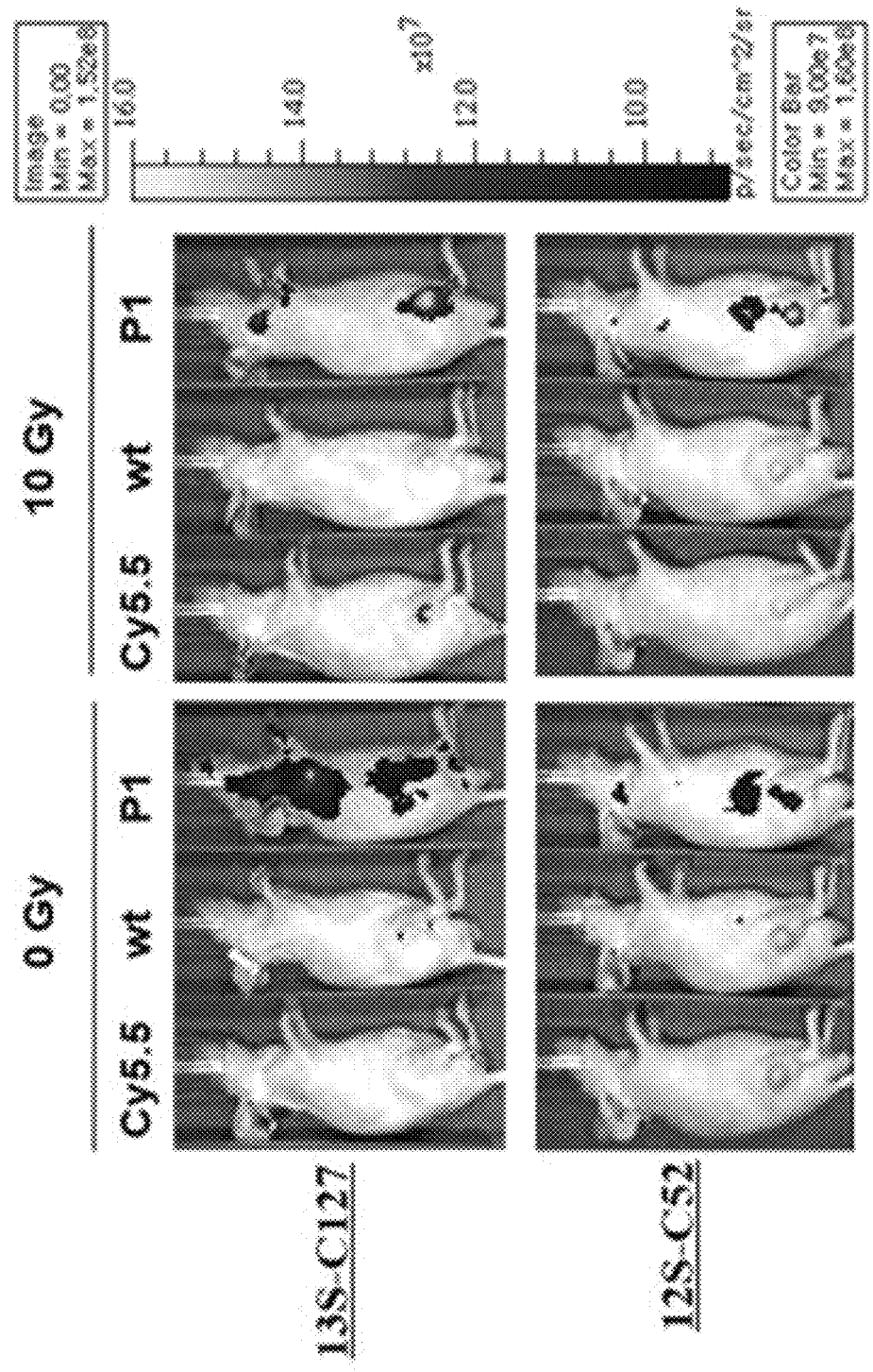
FIG. 13 shows results confirming targeting ability of a selected peptide upon irradiation to mice transplanted with other patient's gastric cancer tissue according to Example 8 of the present invention.

<Example 8> In Vivo Imaging for Verifying Selective Binding Ability of a Peptide Upon Irradiation on a Gastric Cancer Tissue of Other Patients To verify whether the peptide having selective binding ability upon irradiation on the patient's gastric cancer tissue obtained in Examples above also exhibited the same selective binding ability in cases associated with gastric cancer tissues of other patients having the same gastric cancer and the same characteristics upon irradiation, other than the corresponding gastric cancer case showing selective binding of the peptide upon irradiation, gastric cancer tissues each extracted from different patients were prepared to establish a mouse model. In detail, in addition to the patient's gastric cancer tissue used in Example above, two gastric cancer tissues of other patients were prepared, wherein all the gastric cancer tissues used herein were characterized as adenocarcinoma. In the same manner as in Example 1, mouse models including each of the corresponding gastric cancer tissues was established, and some of them were irradiated to thereby establish a control group and an experimental group. According to the in vivo imaging which is the same method as the one used for confirming targeting efficiency in Example 4, the irradiation-dependent targeting efficiency of the peptide was verified. The amplification of phages expressing the selected peptide and the fluorescent labeling were performed in the same manner as in Example 3. Then, the completed sample was injected into each of the irradiated test mouse group and the control group, and images thereof were confirmed on the 2$^{nd}$ day of the observation. As a result, it was confirmed that the two gastric cancer tissues of other patients also showed selective accumulation of peptide-phage only in the tumors of the irradiated test mouse group, in the same manner as in the existing gastric cancer tissue of the patient. The results of the imaging measurement of the corresponding embodiments are shown in FIG. 13. As shown in FIG. 13, it was confirmed that the peptide-expressing phage did not target the cancer tissue when there is no irradiation applied to the cancer tissue, whereas the peptide-expressing phage targeted the cancer tissue when irradiation is applied to the cancer tissue. In conclusion, it was confirmed that the peptide sequence selected in the corresponding technology was clearly verified as the peptide sequence selectively targeting the gastric cancer upon irradiation, and that the targeting ability of the corresponding peptide is not limited to the patient's gastric cancer tissue only. That is, as the peptide sequence exhibiting selective targeting ability only in the case where the gastric cancer tissue of other patients are irradiated, it was verified that the scope of application of the peptide of the present invention is not limited in clinical applications.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A method for diagnosing radio-sensitive gastric cancer, comprising:
    irradiating radiation to a patient having a gastric cancer;
    applying a composition comprising a peptide consisting of amino acid sequence selected from the group consisting of SEQ ID NOs: 1 to 3 to the patient having the gastric cancer;
    detecting the peptide specific to an irradiated gastric cancer tissue; and
    diagnosing the patient as having the radio-sensitive gastric cancer if the peptide being specific to the irradiated gastric cancer tissue is detected.

2. The method of claim 1, wherein the peptide is labeled with one selected from the group consisting of a chromogenic enzyme, a radioactive isotope, a chromopore, and a luminescent or fluorescent material.

3. A method for diagnosing radio-sensitive gastric cancer, comprising:
    obtaining a gastric cancer tissue sample from a patient;
    transplanting the gastric cancer tissue sample into an experimental animal;
    irradiating radiation to the transplanted experimental animal;
    applying a composition comprising a peptide consisting of amino acid sequence selected from the group consisting of SEQ ID NOs: 1 to 3 to the irradiated experimental animal;
    detecting the peptide specific to an irradiated gastric cancer tissue; and
    diagnosing the patient as having the radio-sensitive gastric cancer if the peptide being specific to the irradiated gastric cancer tissue is detected.

* * * * *

SEQUENCE LISTING

<160> NUMBER OF SEQ ID NOS: 6

<210> SEQ ID NO 1
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1

Thr Val Arg Thr Ser Ala Asp
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic peptide

```
<400> SEQUENCE: 2

Arg Tyr Val Gly Thr Leu Phe
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic peptide

<400> SEQUENCE: 3

Asn Arg Gly Asp Arg Ile Leu
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide

<400> SEQUENCE: 4

Asn Trp Gly Asp Arg Ile Leu
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic peptide

<400> SEQUENCE: 5

Gln Arg Ser Leu Pro Ser Leu
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic peptide

<400> SEQUENCE: 6

Asp Val Trp His Ser Ala Tyr
1               5
```